United States Patent [19]

Yan

[11] Patent Number: 5,137,702
[45] Date of Patent: Aug. 11, 1992

[54] REGENERATION OF USED ALKANOLAMINE SOLUTIONS

[75] Inventor: Tsoung Y. Yan, Philadelphia, Pa.

[73] Assignee: Mobil Oil Corporation, Fairfax, Va.

[21] Appl. No.: 525,582

[22] Filed: May 21, 1990

Related U.S. Application Data

[63] Continuation-in-part of Ser. No. 288,392, Dec. 22, 1988, abandoned.

[51] Int. Cl.$^5$ .................. B01D 53/14; C07C 209/84
[52] U.S. Cl. .................................. 423/229; 423/228; 564/497; 210/757
[58] Field of Search .............. 423/228, 229; 564/487, 564/497, 488, 489; 201/2.5; 203/28, 29; 210/766, 757

[56] References Cited

U.S. PATENT DOCUMENTS

| | | | |
|---|---|---|---|
| 3,385,787 | 5/1968 | Crits et al. | 210/673 |
| 3,928,192 | 12/1975 | Katzakian et al. | 210/670 |
| 4,001,386 | 1/1977 | Klein et al. | 423/574 L |
| 4,071,602 | 1/1978 | Pearce | 423/243 |
| 4,138,468 | 2/1979 | Kettner et al. | 423/229 |
| 4,281,200 | 7/1981 | Snoble | 548/229 |
| 4,514,379 | 4/1985 | Miller | 423/229 |
| 4,652,352 | 3/1987 | Saieva | 204/105 R |
| 4,795,565 | 1/1989 | Yan | 210/669 |
| 4,820,421 | 4/1989 | Auerswald | 210/670 |

FOREIGN PATENT DOCUMENTS 1104996 7/1981 Canada .................. 423/228

OTHER PUBLICATIONS

Kennard, M. L.; Meisen, A. "Control DEA Degradation" Hydrocarbon Processing, Apr. 1980, pp. 103-106.
Astarita, G.; Savage, D. W.; Bisio, A. "Gas Treating with Chemical Solvents" Wiley: New York (1984), pp. 439-442.
Meisen & Kennard "DEA Degradation Mechanism", Hydrocarbon Processing, Oct. 1982, pp. 105-108.

Primary Examiner—Michael Lewis
Assistant Examiner—Peter DiMauro
Attorney, Agent, or Firm—Alexander J. McKillop; Charles J. Speciale; Robert B. Furr, Jr.

[57] ABSTRACT

A method is disclosed for regenerating spent alkanolamine solutions containing diethanolamine, to restore their acid gas sorption capacity by converting diethanolamine degradation products to the diethanolamine precursor while avoiding substantial thermal decomposition of diethanolamine.

11 Claims, 1 Drawing Sheet

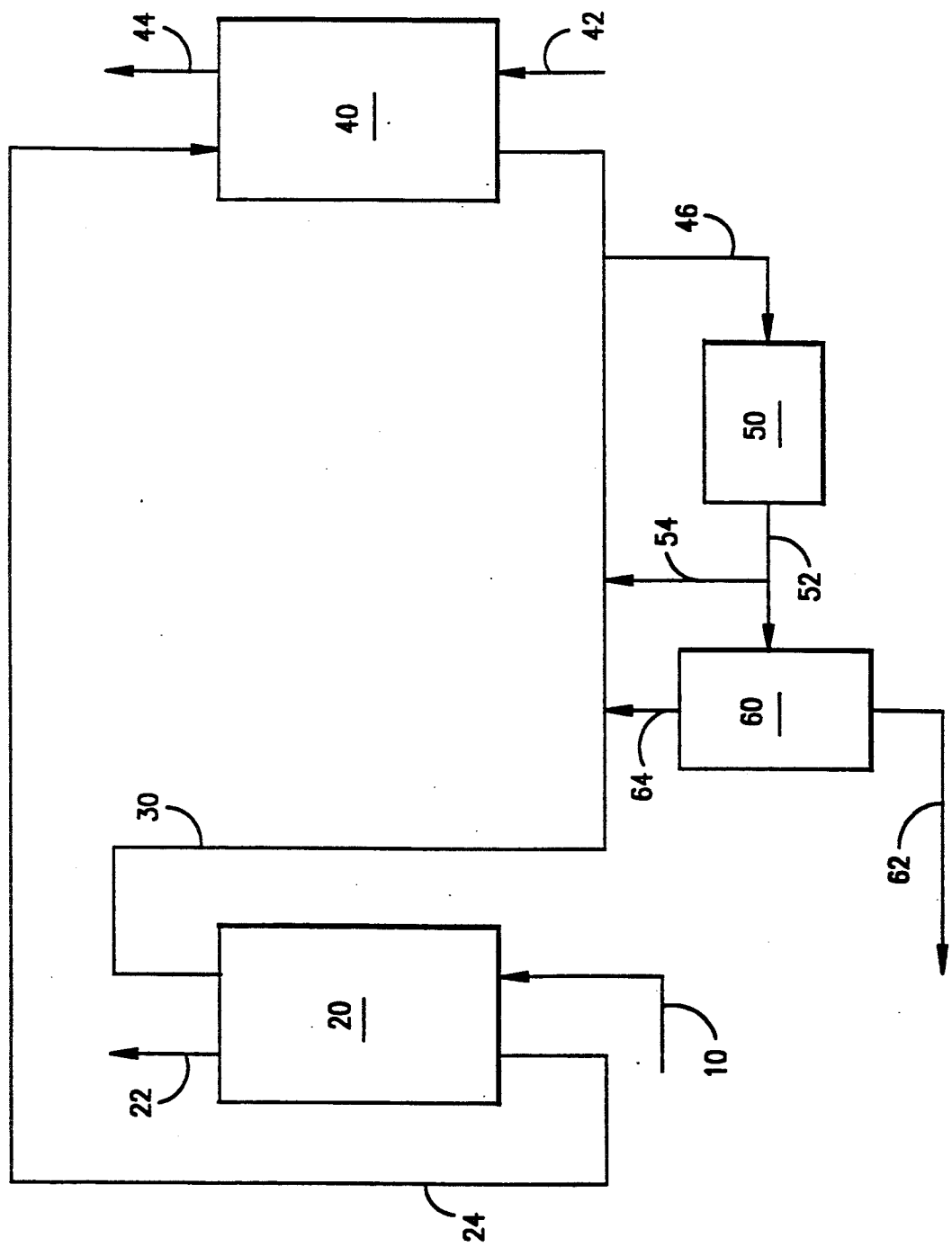

REGENERATION OF USED ALKANOLAMINE SOLUTIONS

The present application is a Continuation-in-Part of commonly assigned U.S. patent application Ser. No. 288,392, filed Dec. 22, 1988, now abandoned.

FIELD OF THE INVENTION

The present invention relates to the regeneration of alkanolamine solutions useful to sorb acid gas constituents from a gas stream. More specifically, the invention relates to a method for treating used alkanolamine solutions to reduce corrosivity and to restore acid gas sorption capacity.

BACKGROUND OF THE INVENTION

Alkanolamine process units remove $H_2S$ and $CO_2$ from gaseous process streams, typically by countercurrently contacting an aqueous solution containing from about 20% to about 50% by weight of an alkanolamine with a gas stream containing $H_2S$ and/or $CO_2$. For the purpose of this application, it is understood that the terms "alkanolamine" and "ethanolamine" are generic terms including, but not limited to, monoethanolamine, diethanolamine, triethanolamine, and methyl diethanolamine.

The removal of hydrogen sulfide from gaseous streams, such as the waste gases liberated in the course of various chemical and industrial processes, for example, in wood pulping, natural gas and crude oil production and in petroleum refining, has become increasingly important in combating atmospheric pollution. Hydrogen sulfide containing gases not only have an offensive odor, but such gases may cause damage to vegetation, painted surfaces and wildlife, and further may constitute a significant health hazard to humans. Government-wide regulations have increasingly imposed lower tolerances on the content of hydrogen sulfide which can be vented to the atmosphere, and it is now imperative in many localities to remove virtually all the hydrogen sulfide under the penalty of an absolute ban on continuing operation of a plant or the like which produces the hydrogen sulfide-containing gaseous stream. Solutions of water and one or more the alkanolamines are widely used in industry to remove hydrogen sulfide and carbon dioxide from such gaseous streams.

Corrosion in alkanolamine units significantly increases both operating and maintenance costs. The mechanisms of corrosive attack include general corrosive thinning, corrosion-erosion, and stress-corrosion cracking. Corrosion control techniques include the use of more expensive corrosion and erosion resistant alloys, continuous or periodic removal of corrosion-promoting agents in suspended solids by filtration, activated carbon adsorption, or by the addition of corrosion inhibitors. (See Kohl, A. L. and Reisenfeld, F. C., *Gas Purification*, Gulf Publishing Company, Houston, 1979, pp. 91-105, as well as K. F. Butwell, D. J. Kubec and P. W. Sigmund, "Alkanolamine Treating", *Hydrocarbon Processing*, March, 1982.)

Further, it has been found that the acid gas sorption capacity in a circulating alkanolamine-water system decreases with time on stream in the absence of added makeup alkanolamine. This performance degradation has been found to be partially attributable to the accumulation of heat stable salts. U.S. Pat. No. 4,795,565 to Yan describes a process for removing heat stable salts from an ethanolamine system by the use of ion exchange resins. The disclosure of U.S. Pat. No. 4,795,565 to Yan is incorporated herein by reference for the operating details both of an ethanolamine acid gas sorption system as well as for the heat stable salt removal process.

Heat stable salts may also be removed from an alkanolamine system by distillation. However, such separation has been limited in the past to relatively mild conditions of temperature and pressure to avoid thermal degradation of the alkanolamine. For example, diethanolamine (DEA) boils at 268° C. at 760 mm Hg pressure and tends to oxidize and decompose at high temperature. For this reason, vacuum distillation has been used to separate heat stable salts from alkanolamine solution.

The chemistry of alkanolamine degradation is discussed in the Butwell et al. article cited above. Briefly, the Butwell et al. article notes that monoethanolamine (MEA) irreversibly degrades to N-(2-hydroxyethyl) ethylene diamine (HEED). HEED shows reduced acid gas removal properties and becomes corrosive at concentrations of at least about 0.4% by weight.

Diglycolamine (DGA), on the other hand, is said to produce a degradation product upon reaction with $CO_2$ which exhibits different properties. DGA is a registered trademark of Texaco, Inc. which identifies an amine having the chemical formula $NH_2-C_2H_4-O-C_2H_4-OH$. DGA degrades in the presence of $CO_2$ to form N,N'-bis(hydroxyethoxyethyl) urea (BHEEU) which is similar to HEED in corrosivity but differs in that BHEEU has no acid gas removal properties.

Diethanolamine (DEA) reacts with $CO_2$ to form N,N'-di(2-hydroxyethyl) piperazine. Unlike HEED and BHEEU, the piperazine compound is noncorrosive and has acid gas removal properties essentially equal to its parent, DEA. See the Butwell et al. article at page 113.

Diisopropylamine (DIPA) readily degrades in the contact with $CO_2$ to form 3-(2-hydroxypropyl) 5-methyl oxazolidone which shows essentially no acid gas removal properties. See the Butwell et al. article at page 113.

U.S. Pat. No. 4,281,200 to Snoble teaches a process for recovering diisopropanolamine from the cyclic reaction products formed by reacting $CO_2$ with diisopropanolamine which process comprises reacting the cyclic product with an inorganic base at temperatures between about 105° and 200° C.

Numerous degradation products formed by the reaction of $H_2S$, or a mixture of $H_2S$ and $CO_2$ with diethanolamine have been reported from analyses of operating diethanolamine acid gas sorption processes and are shown below in Table 1.

TABLE 1

COMPOUNDS RESULTING FROM DEA DEGRADATION

| Name | Abbreviation | Structural formula |
|---|---|---|
| N,N-Bis (2-hydroxyethyl) piperazine | HEP | $HO-CH_2-CH_2-N\begin{smallmatrix}CH_2-CH_2\\ \\CH_2-CH_2\end{smallmatrix}N-CH_2-CH_2-OH$ |

TABLE 1-continued

COMPOUNDS RESULTING FROM DEA DEGRADATION

| Name | Abbreviation | Structural formula |
|---|---|---|
| N,N,N-tris (2-hydroxyethyl) ethylenediamine | THEED | (HO—CH$_2$—CH$_2$)$_2$N—CH$_2$—CH$_2$—NH—CH$_2$—CH$_2$—OH |
| Hydroxyethyl imidazolidone | HEI | cyclic: CH$_2$—CH$_2$—N(CH$_2$CH$_2$OH)—C(=O)—N—(ring) |
| N-Methyldiethanolamine | MDEA | (HO—CH$_2$—CH$_2$)$_2$N—CH$_3$ |
| Oxazolidone | OZO | cyclic: CH$_2$—N(H)—C(=O)—O—CH$_2$ |
| Aminoethylethanolamine | AEEA | NH$_2$—CH$_2$—CH$_2$—NH—CH$_2$—CH$_2$—OH |
| Bis-(2-hydroxy ethyl) glycine | BHG | (HO—CH$_2$—CH$_2$)$_2$N—CH$_2$—C(=O)—OH |

Accumulation of these and other degradation products in the alkanolamine system reduces acid gas sorption capacity and increases the corrosivity of the alkanolamine solution.

SUMMARY OF THE INVENTION

The present invention provides a method for restoring the acid gas sorption capacity and reducing the corrosivity of an alkanolamine solution. Surprisingly, the regeneration of the used alkanolamine solution is effected under elevated temperature conditions which are known to cause oxidation and degradation of aqueous alkanolamine solutions which are relatively free from such impurities.

In a first aspect, the invention comprises a process for regenerating a used aqueous alkanolamine solution to restore its acid gas sorption capacity comprising the steps of:

(a) providing a used aqueous alkanolamine solution containing diethanolamine and a degradation product of said diethanolamine, said degradation product produced by the reaction of H$_2$S and diethanolamine, said degradation product having a lesser affinity for dissolving acid gases such as CO$_2$ and H$_2$S than its diethanolamine precursor;

(b) heating said aqueous alkanolamine solution of step (a) to elevated temperature and holding said aqueous solution of step (a) at said elevated temperature for a period of time sufficient to convert at least a portion of said diethanolamine degradation product to restore the acid gas sorption capacity of said used aqueous alkanolamine solution.

In a second aspect, the invention comprises a process for removing H$_2$S, or both CO$_2$ and H$_2$S from a hydrocarbon gas stream containing the same comprising the steps of:

(a) providing a hydrocarbon gas stream containing a recoverable concentration of H$_2$S, or both CO$_2$ and H$_2$S;

(b) contacting said hydrocarbon gas stream of step (a) with an aqueous alkanolamine solution containing diethanolamine to remove H$_2$S, or both CO$_2$ and H$_2$S from said hydrocarbon gas stream, to convert at least a portion of said diethanolamine to degradation products having a lesser affinity for sorbing acid gases than said diethanolamine, and to evolve an alkanolamine solution enriched in H$_2$S, or both CO$_2$ and H$_2$S;

(c) stripping H$_2$S, or both CO$_2$ and H$_2$S from said enriched alkanolamine solution of step (b) to evolve a lean alkanolamine solution containing both diethanolamine and said diethanolamine degradation products;

(d) heating said lean aqueous alkanolamine stream of step (c) in a regeneration zone to convert diethanolamine degradation products to diethanolamine without substantial thermal decomposition of diethanolamine.

In a third aspect, the invention provides a process for converting the reaction products of H$_2$S and diethanolamine to diethanolamine while avoiding substantial thermal decomposition of diethanolamine comprising the steps of:

(a) reacting H$_2$S with diethanolamine in a first reaction zone to evolve a product mixture containing diethanolamine and diethanolamine degradation products, said product mixture having a lesser affinity for sorbing acid gases than said diethanolamine;

(b) heating the product mixture of step (a) to elevated temperature and holding said heated product mixture in a second reaction zone;

(c) controlling the concentration of diethanolamine degradation products within said second reaction zone to promote conversion of diethanolamine degradation products to diethanolamine while inhibiting the reaction of said diethanolamine to products having a lesser affinity for sorbing acid gases than said diethanolamine.

In accordance with the present invention, it has been found that the acid gas sorption capacity of used alkanolamine solution may be at least partially restored by heating the solution to a temperature of from about 250° to about 750° F. and holding the alkanolamine solution at this temperature for a period of time sufficient to restore the acid gas sorption properties of the alkanolamine solution. Metallic catalysts are useful in the present invention and may comprise one or more metals or metal oxides on a support such as alumina, silica-alumina or a zeolite. The metal may further be present in bulk form, for example as a stainless steel alloy packing material. It is preferable to avoid the addition of bases such as NaOH which tend to form heat stable salts.

The mechanism of this reaction is not understood; however, it is clear that the reaction products exhibit a surprising sorption capacity for acid gases. In fact, the restoration of acid gas sorption capacity upon heating to elevated temperatures contradicts the reasonable expectation that exposure to such temperatures would degrade the alkanolamine solution. While not presented to limit the scope of the present invention by a recitation of theory, this result suggests that some or all of the structures shown in Table 1 react to form the parent diethanolamine under the conditions specified for the present process, and that thermal degradation of the parent diethanolamine is inhibited by the presence of some or all of the compounds shown above in Table 1.

DESCRIPTION OF THE DRAWING

The Figure is a simplified block diagram showing the major processing steps of the present invention.

DETAILED DESCRIPTION

The alkanolamine solution regeneration procedure of the present invention may be conducted in a batch or continuous mode. The continuous mode is preferred, and it is still more preferred to continuously regenerate a slipstream of lean alkanolamine solution comprising from about 1 to about 50% of the total alkanolamine stream by weight, preferably from about 2 to about 20% of the total alkanolamine stream by weight. The relative flow of the slipstream depends on degradation in the acid gas sorption system as well as the allowable level of alkanolamine degradation products in the system.

The regeneration process of the present invention proceeds in the absence of intentionally added catalyst. However, a metallic catalyst may optionally be used. Suitable catalysts include metals in bulk form or dispersed on a support as a heterogeneous catalyst. Useful heterogeneous catalysts include oxides and sulfides of Groups IVA, VA, VIA, VIIA and VIIIA and mixtures thereof on an inert support such as alumina or silica-alumina. Examples of useful metals, metallic oxides and sulfides within these groups are exemplified by sulfides and oxides of titanium, zirconium, vanadium, niobium, tantalum, chromium, molybdenum, tungsten and mixtures thereof. Oxides of chromium alone or in conjunction with other catalytically active species may also be useful. Other catalytically active compounds include sulfides and oxides of manganese, iron, cobalt, rhodium, iridium, nickel, palladium, platinum and mixtures thereof.

The above-listed metals of Groups IVA, VA, VIA, VIIA and VIIIA may also be exchanged onto zeolites to provide a zeolite catalyst having the desired catalytic activity. Additional suitable solid catalysts include MgO, as well as zeolites in their sodium form such as NaX, NaY, NaZSM-5 and Na-mordenites, merely to name a few. Useful catalysts may also include metals in bulk form, for example pure elemental metals or alloys such as chromium-containing stainless steels. Examples of suitable stainless steel alloys include the austenitic alloys such as Types 304, 304L, 309, 310, 316, 316L, 321, and 347, the ferritic stainless steels such as Types 405, 430, 430F, and 446, and the martensitic stainless steels such as Types 403, 410, 414, 416, 420, 431, 440A, 440B, 440C, 501 and 502. As a practical matter, however, the austenitic stainless steels are preferred for ease of fabrication, and the stabilized grade austenitic stainless steels, for example, 321 and 347 are still more preferred for their resistance to stress corrosion cracking.

The bulk metal catalysts are particularly well suited for use in the present invention in the form of reactor packing, e.g. Berl saddles or Raschig rings. Alternatively, the alkanolamine solution may effectively be brought into contact with the bulk metallic catalyst by forming the desired metal or metal alloy into mixing means, e.g., a mixing paddle or static mixing vanes positioned within the reaction zone.

Process Conditions

Broad and preferred reaction conditions useful in the present process are shown below in Table 2.

TABLE 2

| Process Variable | Reaction Conditions Broad | Preferred |
|---|---|---|
| Temperature, °F. | 250–750 | 300–650 |
| LHSV, V/V Hr. | 0.01–100 | 0.1–10 |
| Pressure, psig | –10–2000 | 0–1000 |

Referring now to the Figure, a crude hydrocarbon gas 10 containing one or more acid gases such as $H_2S$, $CO_2$ or both, is charged to alkanolamine absorber column 20, where the crude hydrocarbon gas is countercurrently contacted with lean alkanolamine solution 30 which enters alkanolamine absorber column 20 near the top. The lean alkanolamine solution absorbs the acid gases, purifying the hydrocarbon gas. The purified gas stream 22 is withdrawn overhead from alkanolamine absorber column 20. Upon absorption of the $H_2S$ and $CO_2$, the lean alkanolamine solution 30 becomes a rich ethanolamine solution 34 and is withdrawn from the bottom of alkanolamine absorber column 20.

The rich alkanolamine 34 is then charged to an upper section of a stripper tower 40 and is stripped with steam 42 at about 240° F. to remove the acid gases. Upon stripping, the rich alkanolamine 24 becomes lean alkanolamine 30. A slipstream of lean alkanolamine 46 is drawn off and charged to alkanolamine regeneration reactor 50 where it is held at elevated temperature of about 470° F., preferably in the absence of an added catalyst under relatively mild pressure at liquid hourly space velocity of from about 0.1 to about 10. The reaction pressure is not critical as the regeneration proceeds effectively in both the liquid and gas phases. Reactor 50 may be preceded by a pump and a process heater or heat exchanger to increase pressure and temperature as required to progress the alkanolamine regeneration reaction in the preferred liquid phase. The regenerated alkanolamine solution slip stream 52 may be returned 54 to the lean alkanolamine stream directly or may be processed for removal of heat stable salts. The heat stable salt removal step 60 may comprise distillation, but preferably comprises contacting the lean alkanolamine solution with weak ion exchange resins as taught in U.S. Pat. No. 4,795,565 to Yan, cited above. If a base such as NaOH is added, distillation may be required because the quantity of heat stable salts formed will likely exceed the capacity of readily available ion-exchange facilities. Heat stable salts 62 are then withdrawn from the system for disposal and the purified alkanolamine 64 is returned to the lean alkanolamine stream 30. The lean alkanolamine stream is then recycled to the alkanolamine absorber 20 as described above.

EXAMPLES

EXAMPLE 1

An aqueous, diethanolamine (DEA) solution containing about 20% by weight DEA, 40% by weight other organics including DEA degradation products, and less than about 0.5% by weight total $H_2S + CO_2$ was charged at a rate of 50 cc/hr to a central section a ¾ in. stainless steel column filled with stainless steel Propack Cannon Packings. The column was heated with 3 zones of heaters. The bottom/middle temperature was maintained at 466° F. and the top temperature was 270° F. The system was maintained at a vacuum of 21 inc. of Hg. After 3 hours, the equilibrium condition in the column was established. The overhead and bottom were collected and analyzed for basicity by titration. The following analysis of the products is shown in Table 3, below. Comparison of the feed and product compositions revealed a net loss of NTO and BHEP (structures shown above in Table 1) coupled with a net gain of 19.09 g of DEA, indicating conversion of degradation products to DEA. The recovered overhead exhibited improved acid absorption capacity, indicating that the used DEA solution was successfully regenerated. The acid absorption capacity index (AACI), defined as the sum of the weight percent DEA and one-half (½) the weight percent BHEP, increased more than 40%, from 25.54 to 35.72 upon regeneration in accordance with the present inventive process.

TABLE 3

|  | Product, g | | Feed, g | (Prd.-Feed), g |
|---|---|---|---|---|
|  | Overhead | Residue |  |  |
| DEA | 34.17 | 4.97 | 20.05 | 19.09 |
| BHEP | 3.11 | 1.03 | 10.97 | −6.83 |
| NTO | 6.17 | 1.97 | 28.68 | −20.54 |
| H$_2$O | 38.85 | 4.10 | 36.29 | +6.66 |
| AACI | 35.72 | 5.49 | 25.54 |  |
| Relative AACI | 1.40 |  | 1.0 |  |

EXAMPLE 2

Example 2 demonstrates the beneficial effect of the preferred packed-bed rector. NaOH was added to the lean DEA solution of Example 1 to 1 wt.% level. The feed was pumped downflow through a stainless steel tube filled with stainless steel Propack Cannon packing and the total effluent was collected for analysis. The flow rate was 1 LHSV and the reactor was maintained at the desired temperatures of 522° F. and 473° F. Results are shown below in Table 4 and show conversion of degradation products back to DEA accompanied by an increase of from 53 to 55% in the Acid Absorption Capacity Index (AACI).

TABLE 4

| Temp. °F. | Feed | 522 | 473 |
|---|---|---|---|
| DEA | 22.39 | 42.35 | 39.98 |
| BHEP | 12.04 | 3.42 | 6.76 |
| NTO | 17.58 | 9.73 | 7.26 |
| H$_2$O | 48.00 | 44.50 | 46.00 |
| AACI | 28.41 | 44.06 | 43.36 |
| Relative AACI | 1.0 | 1.55 | 1.53 |

Changes and modifications in the specifically described embodiments can be carried out without departing from the scope of the invention which is intended to be limited only by the scope of the appended claims.

What is claimed is:

1. A process for regenerating a used aqueous alkanolamine solution to restore its acid gas sorption capacity comprising the steps of:
   (a) providing a used aqueous alkanolamine solution containing diethanolamine and a degradation product of said diethanolamine, said degradation product produced by the reaction of $H_2S$ and diethanolamine, said degradation product having a lesser affinity for dissolving acid gases than its diethanolamine precursor;
   (b) heating said aqueous alkanolamine solution of step (a) to elevated temperature, flowing said heated aqueous alkanolamine solution in contact with reactor packing means comprising a metallic catalyst while holding said aqueous solution of step (a) at said elevated temperature for a period of time sufficient to convert at least a portion of said diethanolamine degradation product to restore the acid gas sorption capacity of said used aqueous alkanolamine solution.

2. The process of claim 1 wherein step (b) is carried out in the absence of added base.

3. The process of claim 1 wherein said metallic catalyst comprises stainless steel.

4. The process of claim 3 wherein said stainless steel contains Cr and Ni.

5. The process of claim 4 wherein said stainless steel is an austenitic grade stainless steel.

6. A process for removing $H_2S$, or both $CO_2$ and $H_2S$ from a hydrocarbon gas stream containing the same comprising the steps of:
   (a) providing a hydrocarbon gas stream containing a recoverable concentration of $H_2S$, or both $CO_2$ and $H_2S$;
   (b) contacting said hydrocarbon gas stream of step (a) with an aqueous alkanolamine solution containing diethanolamine to remove $H_2S$, or both $CO_2$ and $H_2S$ from said hydrocarbon gas stream, to convert at least a portion of said diethanolamine to degradation products having a lesser affinity for sorbing acid gases than said diethanolamine, and to evolve an alkanolamine solution enriched in $H_2S$, or both $CO_2$ and $H_2S$;
   (c) stripping $H_2S$, or both $CO_2$ and $H_2S$ from said enriched alkanolamine solution of step (b) to evolve a lean alkanolamine solution containing both diethanolamine and said diethanolamine degradation products;
   (d) heating said lean aqueous alkanolamine stream of step (c) in a regeneration zone and flowing said heated lean aqueous alkanolamine stream in contact with reactor packing means comprising a metallic catalyst to convert diethanolamine degradation products to diethanolamine without substantial thermal decomposition of diethanolamine.

7. The process of claim 6 wherein step (b) is carried out in the absence of added base.

8. The process of claim 6 wherein said metallic catalyst comprises stainless steel.

9. The process of claim 8 wherein said stainless steel contains Cr and Ni.

10. The process of claim 9 wherein said stainless steel is an austenitic grade stainless steel.

11. A process for converting the reaction products of $H_2S$ and diethanolamine to diethanolamine while avoiding substantial thermal degradation of diethanolamine comprising the steps of:

(a) reacting $H_2S$ with diethanolamine in a first reaction zone to evolve a product mixture containing diethanolamine and diethanolamine degradation products, said product mixture having a lesser affinity for sorbing acid gases than said diethanolamine;

(b) heating the product mixture of step (a) to elevated temperature and flowing said heated product mixture in contact with reactor packing means comprising a metallic catalyst in a second reaction zone;

(c) controlling the concentration of diethanolamine degradation products within said second reaction zone to promote conversion of diethanolamine degradation products to diethanolamine while inhibiting the reaction of said diethanolamine to products having a lesser affinity for sorbing acid gases than said diethanolamine.

* * * * *